United States Patent
Campo et al.

(12) 
(10) Patent No.: US 6,174,532 B1
(45) Date of Patent: *Jan. 16, 2001

(54) L2 IMMUNOGENIC PEPTIDES OF PAPILLOMAVIRUS

(75) Inventors: Maria Saveria Campo, Glasgow; William Fleming Hogan Jarrett, Blanefield, both of (GB)

(73) Assignee: Cancer Research Campaign Technology Limited, London (GB)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/817,548
(22) PCT Filed: Oct. 6, 1995
(86) PCT No.: PCT/GB95/02372
  § 371 Date: May 12, 1997
  § 102(e) Date: May 12, 1997
(87) PCT Pub. No.: WO96/11273
  PCT Pub. Date: Apr. 18, 1996

(30) Foreign Application Priority Data

Oct. 6, 1994 (GB) .................................... 9420146

(51) Int. Cl.⁷ ............................ A61K 39/12; A61K 38/00
(52) U.S. Cl. .................................... 424/204.1; 424/186.1; 424/192.1; 435/69.1; 435/69.3; 530/300; 536/23.72; 536/23.4
(58) Field of Search ............................ 424/204.1, 192.1, 424/186.1; 435/69.1, 69.3, 320.1, 236; 530/300; 536/23.72, 23.4

(56) References Cited

U.S. PATENT DOCUMENTS 5,618,536 * 4/1997 Lowy et al. .................. 424/192.1

FOREIGN PATENT DOCUMENTS

| 0 133 123 A1 | 2/1985 | (EP) . |
| 0 375 555 A1 | 6/1990 | (EP) . |
| WO 86/05816 | 10/1986 | (WO) . |
| WO 90/04790 | 5/1990 | (WO) . |
| WO 93/00436 | 1/1993 | (WO) . |

OTHER PUBLICATIONS

Zhou et al, Feb. 1994, J. of Virology, vol. 68 (2), pp. 619–625, 1997.*

Yaegashi et al, Mar. 1991, J. of Virology, vol. 65 (3), pp. 1578–1583, 1991.*

Lin, et al., Effective Vaccination against Papilloma Development by Immunization with L1 or L2 Structural Protein of Cottontail Rabbit Papillomavirus, Virology 187, 612–619 (1992).

Chandrachud, et al., Humoral Immune Response to the E7 Protein of Bovine Papillomavirus Type 4 and Identification of B–Cell Epitopes, Virology, 200, 98–104 (1994).

Christensen, et al., The Open Reading Frame L2 of Cottontail Rabbit Papillomavirus Contains Antibody–Inducing Neutralizing Epitotpes, Virology 181, 572–579 (1991).

Campo et al., Prophylactic and therapeutic vaccination against a muscosal papillomavirus, Journal of General Virology 74, 945–953 (1993).

Boswell et al, 1988, Oxford University Press, pp. 161–178, 1988.*

* cited by examiner

*Primary Examiner*—Ali Salimi
(74) *Attorney, Agent, or Firm*—Klarquist Sparkman Campbell Leigh & Whinston, LLP

(57) ABSTRACT

The N-terminal region of bovine papillomavirus (BPV-4) L2 protein includes three immunogenically active epitopes. Two of these epitopes have substantial sequence homology to human papillomavirus (HPV) types. The BPV and HPV sequences are used to produce vaccine formulations for use in cattle and humans.

21 Claims, 8 Drawing Sheets

Figure 1:
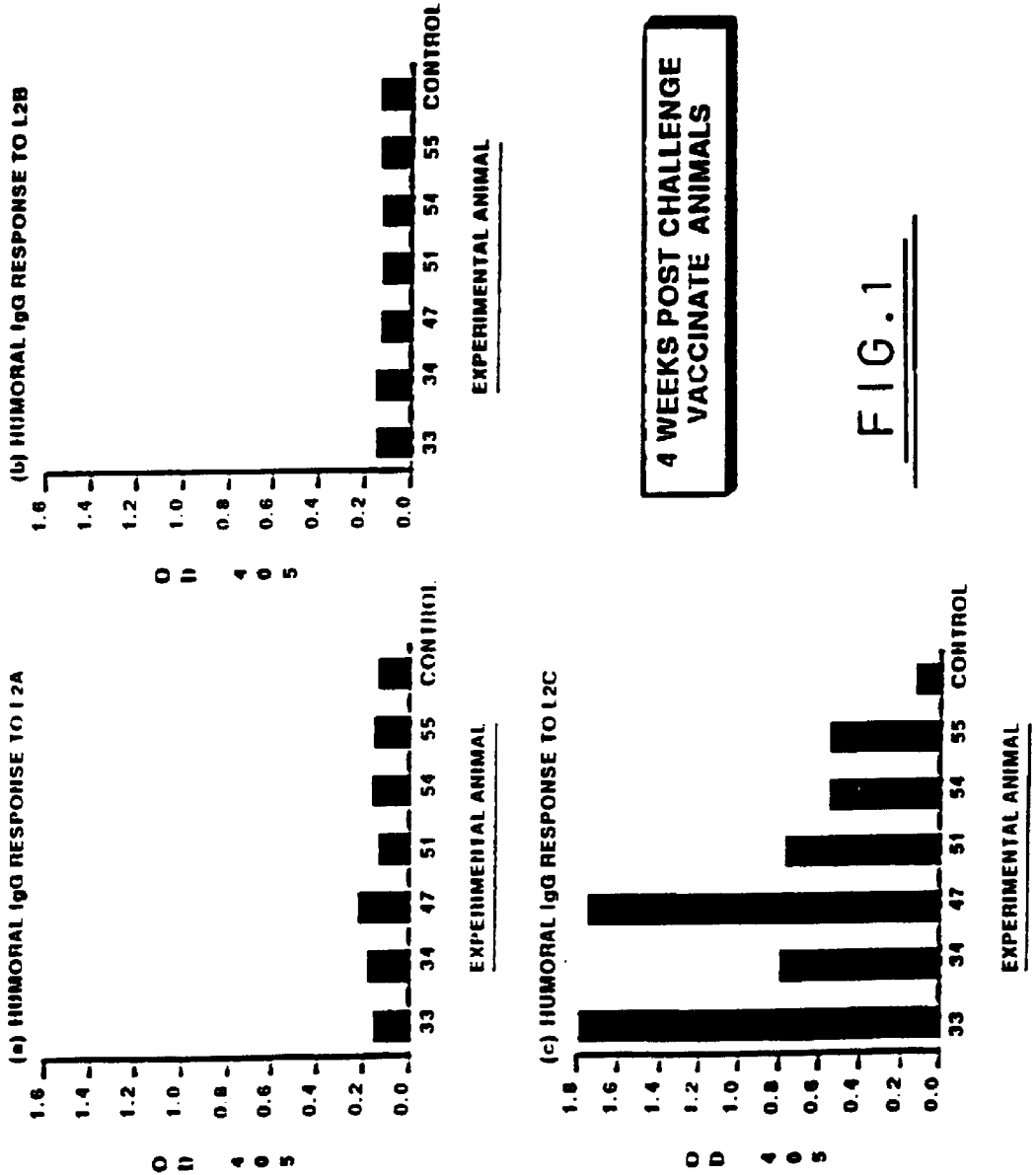

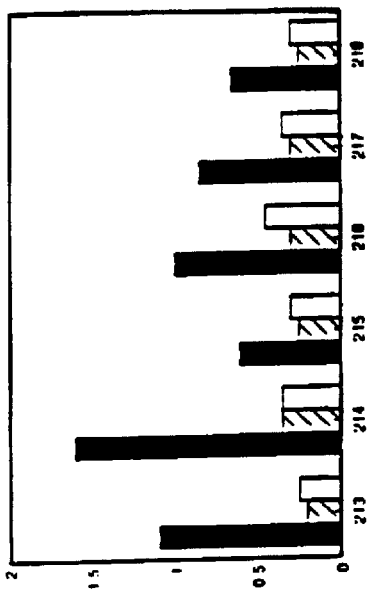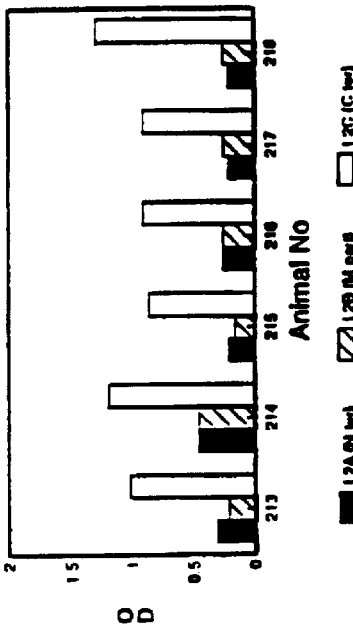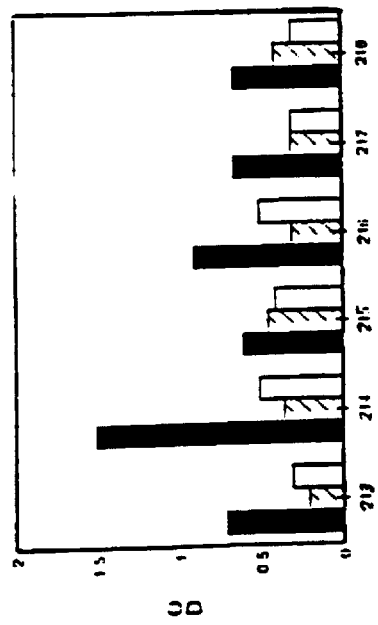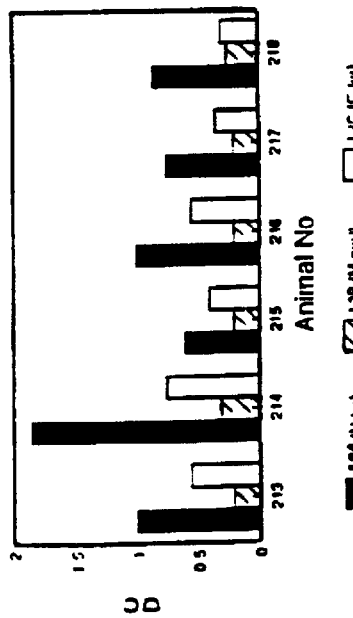
FIG. 3

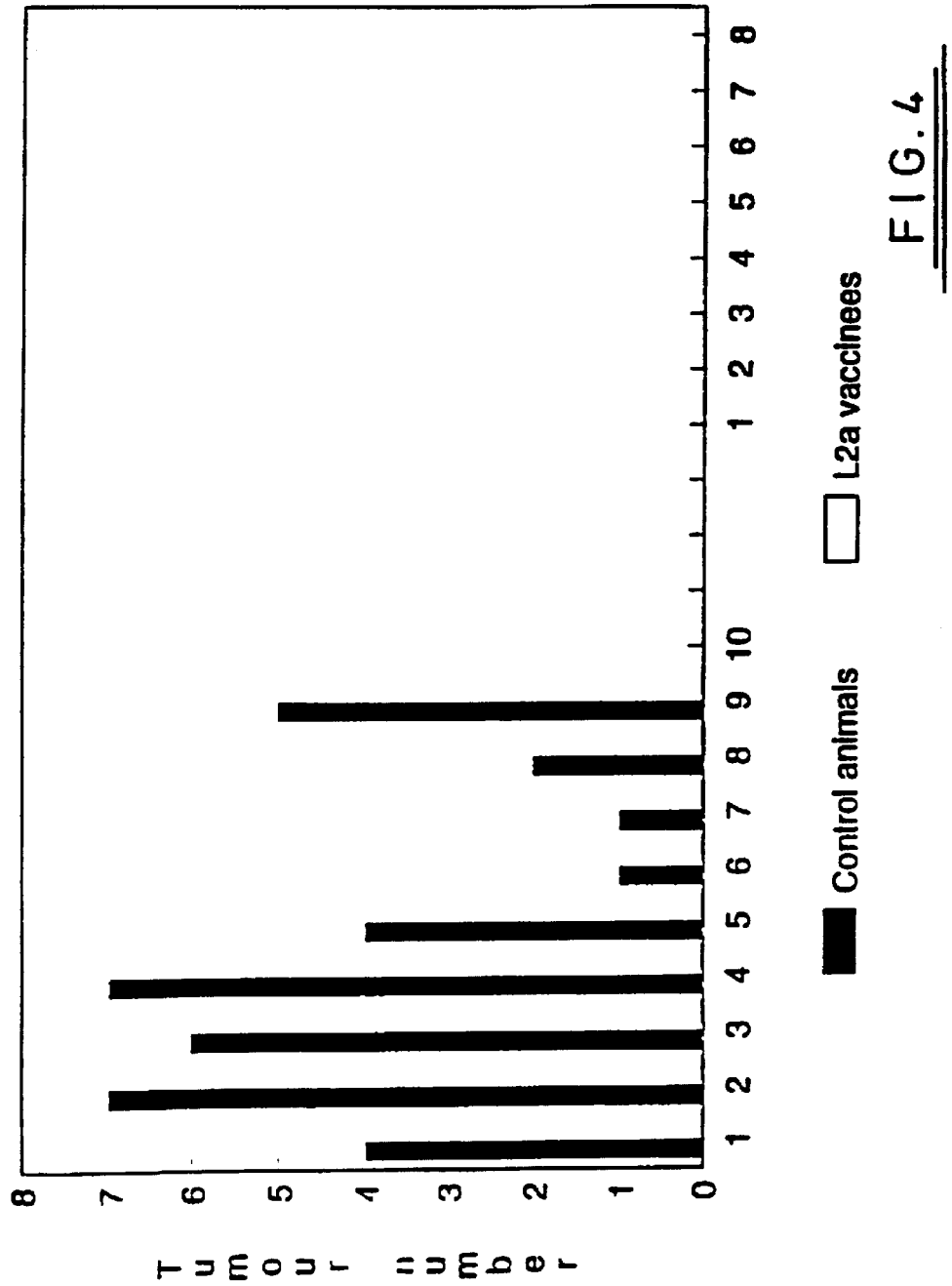

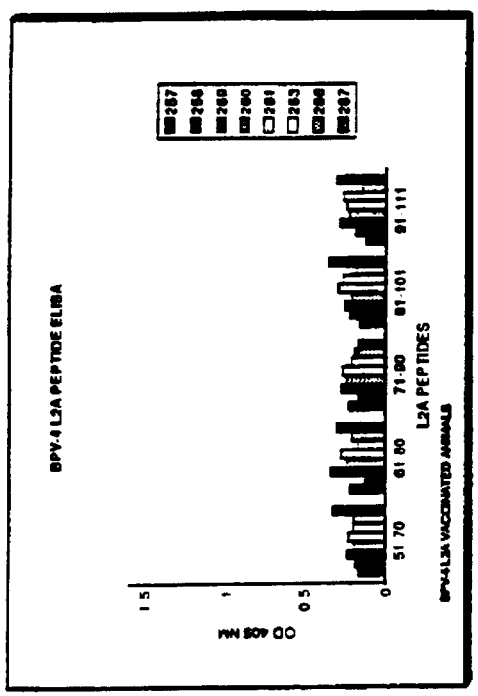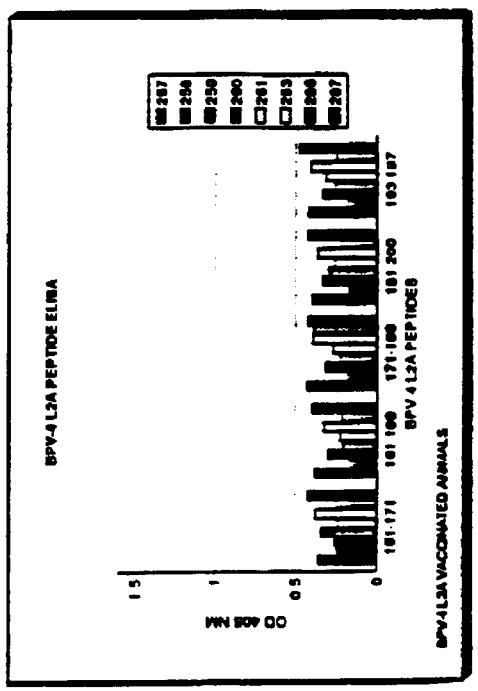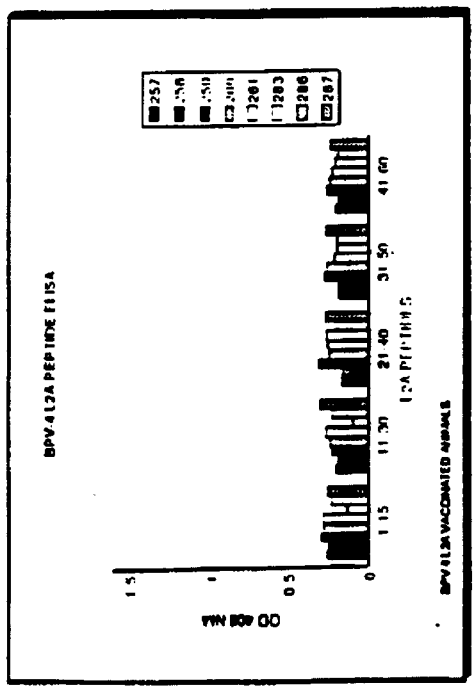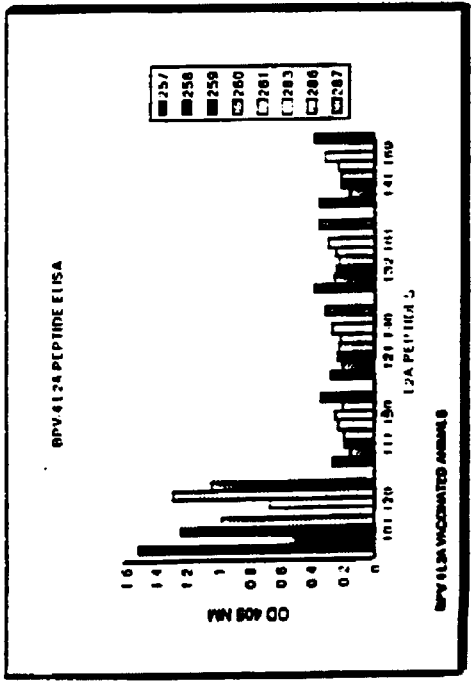
FIG. 5A (I) BPV Peptide 11 (101-120)

1  THR GLY VAL PRO ILE ASP PRO ALA VAL PRO  10
11 ASP SER SER ILE VAL PRO LEU LEU GLU SER  20

(II) BPV Peptide 14 (132-151)

1  GLY ALA GLU ILE GLU ILE ILE ALA GLU VAL  10
11 HIS PRO PRO VAL TYR GLU GLY PRO GLU  20

(III) BPV Peptide 16 (151-171)

1  VAL THR ILE GLY ASP ILE GLU GLU PRO PRO  10
11 ILE LEU GLU VAL VAL PRO GLU THR HIS PRO  20
21 THR

FIG.7

L2 IMMUNOGENIC PEPTIDES OF PAPILLOMAVIRUS

RELATED APPLICATIONS

This application claims priority to International Application No. PCT/GB95/02372, filed Oct. 6, 1994, which is based on British Application No. GB 9420146.4, filed Oct. 6, 1994.

FIELD OF THE INVENTION

The present invention relates to the use of papillomavirus L2 protein fragments in medicine. In particular the invention relates to vaccine preparations for immunisation against papillomavirus and papillomavirus related diseases in mammals, particularly humans and cattle.

BACKGROUND OF THE INVENTION

Papillomaviruses induce a variety of lesions both in humans and in animals. Some papillomas, albeit benign, are themselves a clinical problem, such as laryngeal papillomas of children (Steinberg and Abramson, 1985) or penile papillomas of bulls (Jarrett, 1985a), and others are known to be a risk factor in the pathogenesis of cancer, as in the case of flat lesions of the cervix or penile condylomata in humans (zur Hausen, 1978). Therefore both in human and veterinary medicine the introduction of an anti viral vaccine, would be of major importance.

International Patent Application No. PCT/GB 92/01092 relates to the use of papillomavirus L2 protein as a therapeutically effective component in the treatment of papillomavirus tumours or lesions. In the examples, it is stated that the L2 open reading frame (ORF) of BPV-4 was cloned as the whole L2 ORF (encoding amino acids—8 to 525) and as three fragments encoding amino acids 11 to 201, 203 to 329 and 330 to 525. In subsequent vaccination experiments mixtures of the above amino acid sequence fragments were used in vaccination compositions. However, the identification of the active fraction capable of conferring immunity to papillomavirus and by extension to papillomavirus related diseases was not attempted. Other workers have reported that the L2 protein of cottontail rabbit papillomavirus (CRPV) is a prophylactic vaccine in rabbits [Christensen et al., Virology, (181, pp 572–579 (1991); Lin et al., Virology, 187, pp 612–619 (1992)] and the L2 protein of BPV-4 in cows (Campo et al, J.gen.virol. 74, pp 945–953 (1993). Christensen et al used the terminal carboxyl half of the L2 protein (amino acids 259–492) of CRPV and Lin et al used an L2 protein of CRPV from amino acid number 67-489. Neither group suggested employing a polypeptide comprising a portion corresponding to the active N-terminus of BPV-4 L2 (amino acids 11–200). Further workers, expressed the complete BPV-1 L1 and L2 proteins in E. Coli. The L1 protein was used to vaccinate calves and this resulted in a degree of protection from challenge with BPV-1 (Pilacinski et al., Papillomaviruses: Molecular and Clinical Aspects, UCLA Symposium 2, (1985), pp 257–271). It was also reported that rabbit antisera raised against L1 or L2 were capable of neutralising BPV-1 in transformation assays of C127 mouse cells, implying that both L1 and L2 contained neutralising epitopes. This was not tested in cows. Furthermore, only one in five rabbit L2 immune sera tested could neutralise the virus.

However, the prior art does not indicate which element of the papillomavirus L2 protein is the immunogenic element responsible for effective prophylactic therapy, though the work of Christensen et al. and Lin et al. would incline the skilled worker to expect the immunogenic epitope to lie within the carboxy-terminal portion of the peptide. Vaccines produced to date are generally made up of mixtures of various fusion proteins (if produced via recombinant DNA technology) or are of crude extracts of papillomavirus elements or are made up of live virus strains which may display an immunogenic activity in an animal species but which activity may or may not be readily reproducible. Such extracts used as vaccines have not generally been found to work well when applied to other species and do not appear to be particularly efficient.

It is an object of the present invention to provide a more effective prophylactic vaccine against papillomavirus infection in mammals.

It is a further object of the invention to provide a more efficient immunogenically active component for use in a prophylactic treatment of papillomavirus infection.

These and other objects will become apparent from the following description and examples.

SUMMARY OF THE INVENTION

It has now surprisingly been found that the immunogenic epitope or epitopes of the L2 protein lie within the N-terminal region, contrary to preliminary work (as described herein) and expectations of the present inventors and the inferences to be drawn from the teachings of the prior art. Thus, the N-terminal fragment of papillomavirus L2 (e.g. amino acids 11–200) or part thereof can help prevent the occurrence of disease states in mammals which are susceptible to papillomavirus infection.

Furthermore, it has been found that at least some of the epitopes found in the N-terminal region display a remarkable sequence similarity to the corresponding fragment of human papillomavirus types. Thus, the present invention provides the use of the N-terminal portion of papillomavirus L2 protein or a prophylactically effective peptide fragment thereof (or a prophylactically effective peptide derivative sequence thereof) in the production of a medicament suitable for use as a prophylactic agent against papillomavirus infection in mammals (which includes humans).

The peptide fragment can be upto about 200 amino acids long, preferably from about 10 to 200 amino acids long, more preferably from about 10 to 30 amino acids long, and most preferably about 10 to 20 amino acids long. In embodiments of the invention the immunogenically effective peptide fragment includes as a part thereof one of the following amino acid sequences (referred to as SEQ. ID NO:1, SEQ. ID NO:2 and SEQ. ID NO:3 reading from N-terminus to C-terminus and in particular the underlined amino acid fragment; or derivatives thereof so long as such derivatives of the peptide(s) has/have a prophylactic activity.

```
 1  THR GLY VAL PRO ILE ASP PRO ALA VAL PRO 10   SEQ ID NO:1

11  ASP SER SER ILE VAL PRO LEU LEU GLU SER 20
```

```
                                -continued
1  GLY ALA GLU ILE GLU ILE ILE ALA GLU VAL 10   SEQ ID NO:2

11 HIS PRO PRO VAL TYR GLU GLY PRO GLU 20

1  VAL THR ILE GLY ASP ILE GLU GLU PRO PRO 10   SEQ ID NO:3

11 ILE LEU GLU VAL VAL PRO GLU THR HIS PRO 20

21 THR
```

Without the intention of being bound by theory it is thought that the above amino acid sequences (and particularly the underlined fragments) may not be capable of eliciting an immune response per se, but are generally required to be included as a part of a larger protein if a satisfactory immune response is to be obtained. The amino acid sequence may thus be part of a native papillomavirus L2 sequence, or a synthetically derived like sequence thereto, or may be conjugated or fused to another protein or peptide such as keyhole limpet haemocyanin (KLH) (for rabbits) or glutathione-S-transferase (GST).

Thus, the invention also includes isolated or synthetically prepared peptides which are capable of prophylactic function and therefore possess an appropriate immunogenic capacity.

For the purposes of the present invention a derivative of a sequence of the invention is one which is capable of eliciting a prophylactic effect in a mammal. Preferably such a derivative retains a recognisable degree of similarity with respect to one of the L2 sequences shown hereinabove. Thus, substitutions, additions, deletions or combinations thereof can be made in the sequence of amino acid residues provided that any resultant sequence is capable of eliciting a prophylactic effect in an appropriate protein, polypeptide, or peptide format. Focusing on the ca 20 amino acid residue long BPV-L2 sequences (I) and (III) per se, the degree of similarity with an amino acid residue sequence under comparison can be from about 20% to about 35%, preferably from 30% to 35% on the basis of amino acid identity and conservative replacement of amino acid residues in a like position when aligned optimally; For instance, allowing for at least the underlined amino acids in the SEQ ID NO:1, or the underlined amino acids of SEQ ID NO:3 showing substantial similarity with a 10 or 14 amino acid residue sequence to which they have been aligned; or similarity may be up to about 55% or more, preferably from about 40% to about 50% where the possibility of amino acid replacement on the basis of physico-chemical similarity is also included.

Such peptides can exhibit sequence similarities with other papillomavirus types such as human papillomaviruses e.g. HPV-18, HPV-16, HPV-11, HPV-6 and the like.

Thus, for instance, over the underlined amino acids of the C-terminus end of SEQ ID NO:1 shown above, the degree of similarity with a corresponding 10 amino acid residue long peptide portion thereto can be from 40% to about 70%, preferably from about 60% to about 70% on the basis of amino acid identity and conservative replacement of amino acid residues; may be from about 80% to about 100% where the possibility of replacement on the basis of physico-chemical similarity is also included.

Naturally, the skilled addressee will appreciate that there are computer programs available in the art which are able to make alignments between different amino acid sequences. An example of such a program is BESTFIT of TRANSLATE in the Genetic Computer Group (University of Wisconsin) package.

For the purpose of the present invention conservative replacements may be made between amino acids within the following groups:

(i) Alanine, serine and threonine.

(ii) Glutamic acid and aspartic acid.

(iii) Isoleucine, leucine, valine and methionine.

Thus, where amino acid residue substitution, additions and/or deltions are made, any resultant peptide should substantially retain an immunogenic potential similar to that of the naturally occurring epitope as described above. Examples of such allowable modification in amino acid residues which do not go to conservative replacement of amino acid residues or to identity as such include for example, proline for serine and serine for glutamic acid.

Examples of at least 10 amino acid residue long peptide sequences and of 14 amino acid long peptide sequences which can be optimally aligned using an appropriate computer program as described above (e.g. Bestfit of Translate) and are capable of being included in a peptide, polypeptide or protein format capable of an immunogenic potential include HPV-18, HPV-16, HPV-11 and HPV-6 as shown hereinbelow:

```
THR ASP PRO SER ILE VAL THR LEU ILE GLU HPV-18                    (SEQ ID NO.4)

SER ASP PRO SER ILE VAL SER LEU VAL GLU HPV-16                    (SEQ ID NO.5)

SER ASP PRO SER ILE VAL SER LEU ILE GLU HPV-11                    (SEQ ID NO.6)

SER ASP PRO SER ILE VAL SER LEU ILE GLU HPV-6                     (SEQ ID NO.7)

SER ASP PRO SER ILE VAL SER LEU ILE GLU CONSENSUS                 (SEQ ID NO.8)

HPV-18 ILE THR SER ALA GLY THR THR THR PRO ALA VAL LEU ASP ILE    (SEQ ID NO.9)

HPV-16 ILE THR THR SER THR ASP THR THR PRO ALA ILE LEU ASP ILE    (SEQ ID NO.10)

HPV-11 ILE THR SER SER GLU SER THR THR PRO ALA ILE LEU ASP VAL    (SEQ ID NO.11)
```

```
                                            -continued

HPV-6   ILE THR SER SER GLU THR THR THR PRO ALA ILE LEU ASP VAL      (SEQ ID NO.12)

CONSENSUS

ILE THR SER SER GLU THR THR THR PRO ALA ILE LEU ASP VAL      (SEQ ID NO.13)
```

SEQ ID NO:2 of BPV in fact has no significant homology to any of the above human papilloma viruses.

Thus in a further aspect of the invention there is provided an immunogenic peptide capable of eliciting an immunogenic response in humans which includes a sequence corresponding to any of the ten HPV SEQ ID Nos. 4, 5, 6, 7, 8, 9, 10, 11, 12, and 13 listed above.

Preferably, said L2 fragment comprises a 35% similarity in respect of SEQ ID NO:1, SEQ ID NO:2 and SEQ ID NO:3, when conservative amino acid residue replacement is taken into account. Thus, the papillomavirus L2 peptide fragment may be a bovine papillomavirus L2 fragment or a human papillomavirus L2 fragment or derivatives thereof.

Thus, in a further embodiment of the invention there are provided peptide sequences capable of eliciting an immune response in mammals comprising at least a 60% identity with the underlined portions of the BPV-4 L2 peptide fragment of SEQ ID NO:1 and 43% identity with the underlined portion of SEQ ID NO:3.

The invention also provides for an isolated prophylactically effective peptide fragment comprising the N-terminal portion of a papillomavirus L2 protein. The isolated prophylactic effective peptide fragment will approximate the same size of the fragment as described herein above.

Naturally, the invention further provides for any corresponding nucleotide sequence to the isolated peptide fragment or to any peptide fragments capable of being used to give rise to immunogenic peptides of the invention.

The invention also provides a pharmaceutical formulation for the prophylactic therapy of papillomavirus infection, which comprises an N-terminal L2 peptide of at least about 10 amino acids in length in admixture with a pharmaceutically acceptable carrier. Preferably, the peptide is of the order of 20 amino acids in length and has at least 30% identity with an N-terminal BPV L2 and/or HPV L2 peptide.

Generally speaking, the prophylactic effect of the N-terminal L2 peptide fragment may be limited to the respective papillomavirus type, for example, in humans, HPV-18, HPV-16, HPV-11, and HPV-6. Thus, for general pophylactic applications in mammals, such as in humans and/or cows where the particular papillomavirus type or types to be vaccinated against may be unidentified, it may be desirable to employ a mixture or cocktail of different N-terminal L2 peptide fragments as hereinbefore described.

The prophylactic therapy will be applicable to papillomavirus infection of mammals, including humans and cows. In humans, the invention is particularly applicable for prophylactic therapy not only against papilloma infection per se, but also for secondary diseases caused directly or indirectly as a result of papillomavirus infection. Such disease types may include laryngeal tumours, skin tumours and genital lesions, whether malignant or not. In cows, the therapy is particularly useful for prophylactic treatment against such ailments as udder and teat warts or prevention of papillomavirus infection in the alimentary canal.

The L2 N-terminus fragment is generally produced by recombinant DNA techniques. In particular, a plasmid containing the papillomavirus L2 pen reading frame (ORF) or a derivative thereof as described above may be molecularly cloned into a bacterial expression vector which may then be used to transfect into an appropriate bacterial host such as E. coli., and cultured. As alluded to above, different peptide fragments of the N-terminus of the L2 protein may be produced providing that the therapeutic prophylactic effectiveness of such fragments is substantially unimpaired. The N-terminus L2 fragment may be administered in the form of a suitable fusion protein, such as one produced by E. coli, e.g. glutathione-S-transferase-L2, in a pharmaceutically acceptable vaccine formulation. Alternatively, the L2 fragment may be cleaved from its fusion partner protein and admixed by itself in a suitable pharmaceutically acceptable formulation. In all cases of administration the L2 fragment should be capable of giving rise to an immunogenic effect leading to a degree of immunisation.

Thus N-terminal L2 peptide fragments may be in the native form, with additions, deletions or substitutions which do not substantially affect therapeutic prophylactic effectiveness. Alternatively N-terminal L2 peptide fragments may be in synthetic form (produced by direct peptide synthesis) with additions, deletions or substitutions which do not substantially affect therapeutic prophylylactic effectiveness.

The N-terminus L2 protein fragment (or immunogenic nucleotide sequence) will usually be administered in the form of a pharmaceutical formulation. The formulation contains a pharmaceutically acceptable carrier. The carrier must be acceptable in the sense of being compatible with the other components of the formulation and not deleterious to the recipient thereof.

Since the N-terminus L2 protein fragment is broken down in the stomach, oral administration is not preferred. The pharmaceutical formulation is preferably formulated for parenteral administration, including subcutaneous, intramuscular and intravenous injection; or as a suppository or pessary. For parenteral administration the formulation may be presented as a sterile solution or suspension in a suitable liquid vehicle, which may also contain preservatives and materials for rendering the formulation isotonic. The formulations may be presented in unit dose or multi-dose containers. The carrier will generally be apyrogenic. Each dose will generally contain 100 to 10,000 micrograms of the L2 protein fragment. In order to enhance the prophylactic effect of the protein fragment, it may be administered together with an adjuvant, such as Freund's incomplete adjuvant, as an oil-in-water emulsion or using other adjuvant systems known in the art such as L101 and DDA as used in Pilacinski et al (1986): Immunisation against bovine papillomavirus infection. Ciba Foundation Symposium 120; Papillomaviruses pp 136–148.

DESCRIPTION OF PREFERRED EMBODIMENTS

Embodiments of the present invention will now be described by way of example only with reference to the following experimental protocols. Peptide L2a illustrates the present invention. Results for L2b and L2c proteins are shown for comparison purposes only.

FIG. 1: Shows the antibody response in immune sera from animals vaccinated with L2 protein fragments against the N-terminus protein fraction L2a, the middle portion L2b, and the C-terminus L2c of the vaccine protein at 4 weeks after challenge to determine the immunologically active portion of the protein.

Figure 2:
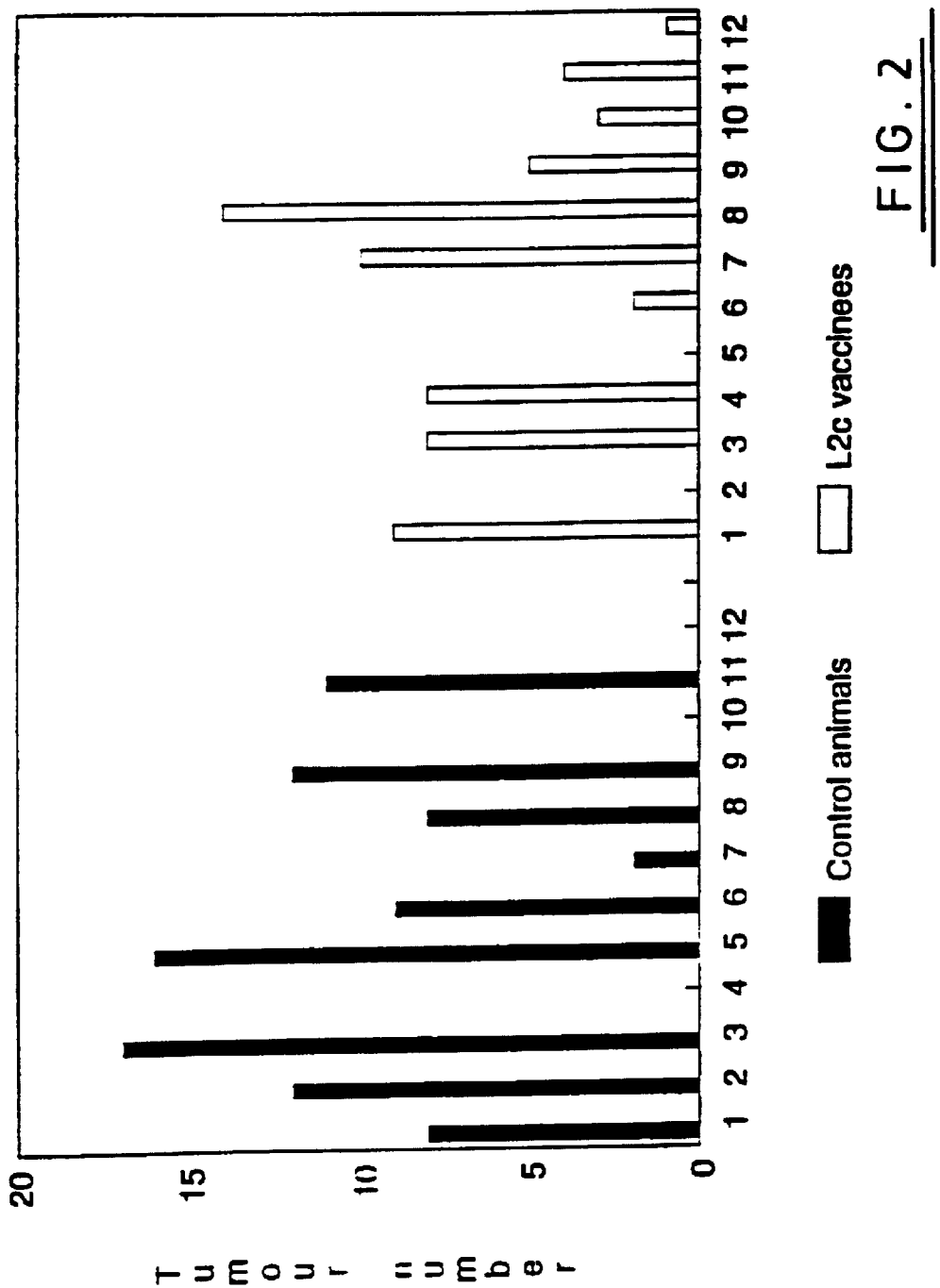

FIG. 2: Shows the results of a bovine papillomavirus-4 L2c vaccine for comparison purposes.

FIG. 3: Shows the results of analysing for antibodies to L2a, L2b and L2c over a time course of up to 14 days after virus challenge.

FIG. 4: Shows that all L2a (the present invention) vaccinated animals are resistant to BPV-4 infections.

Figure 5B:
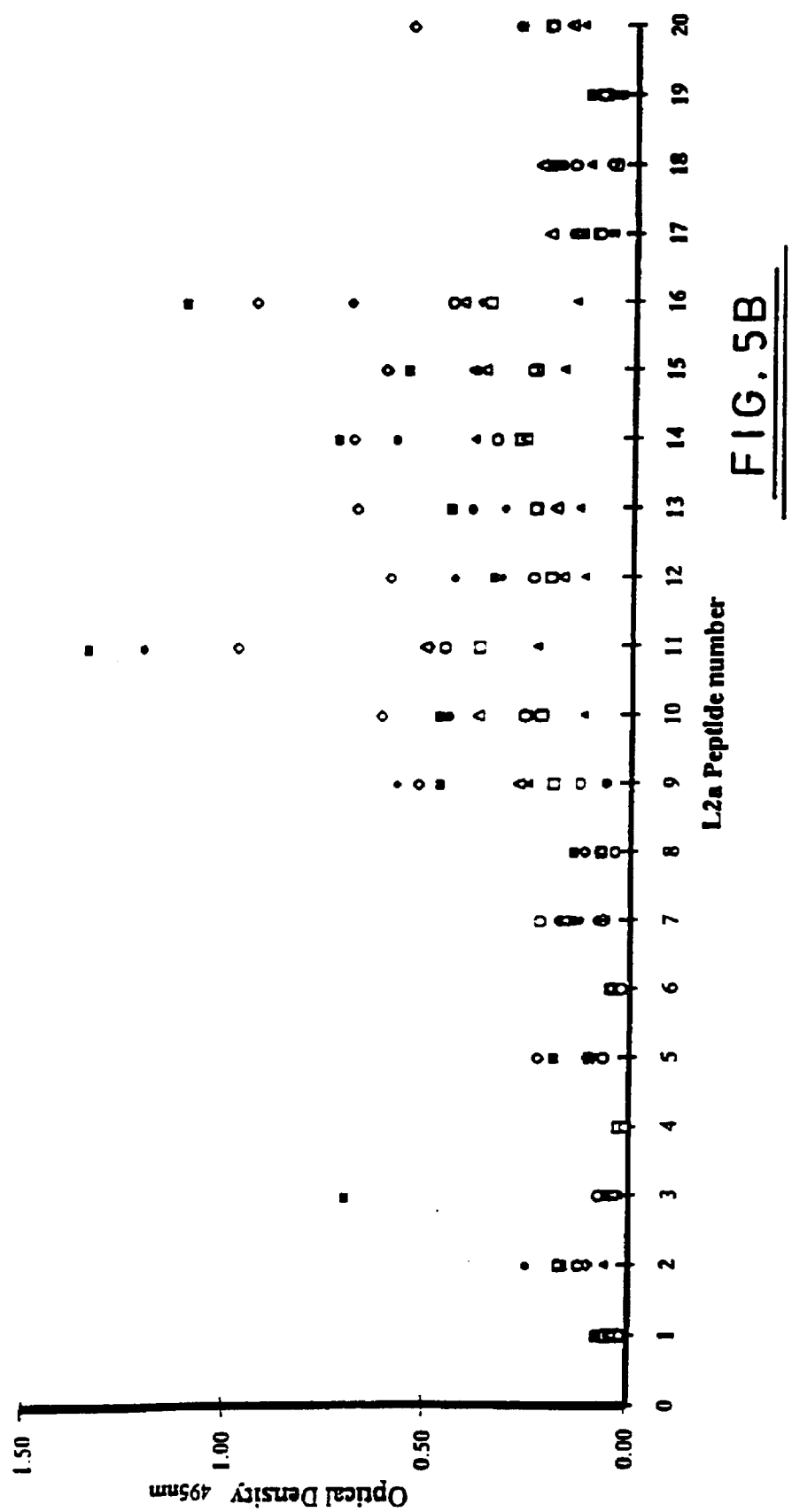

FIGS. 5A and 5B: Show the presence of three immunodominant B-cell epitopes encoded by the N-terminus of the L2 protein.

Figure 6:
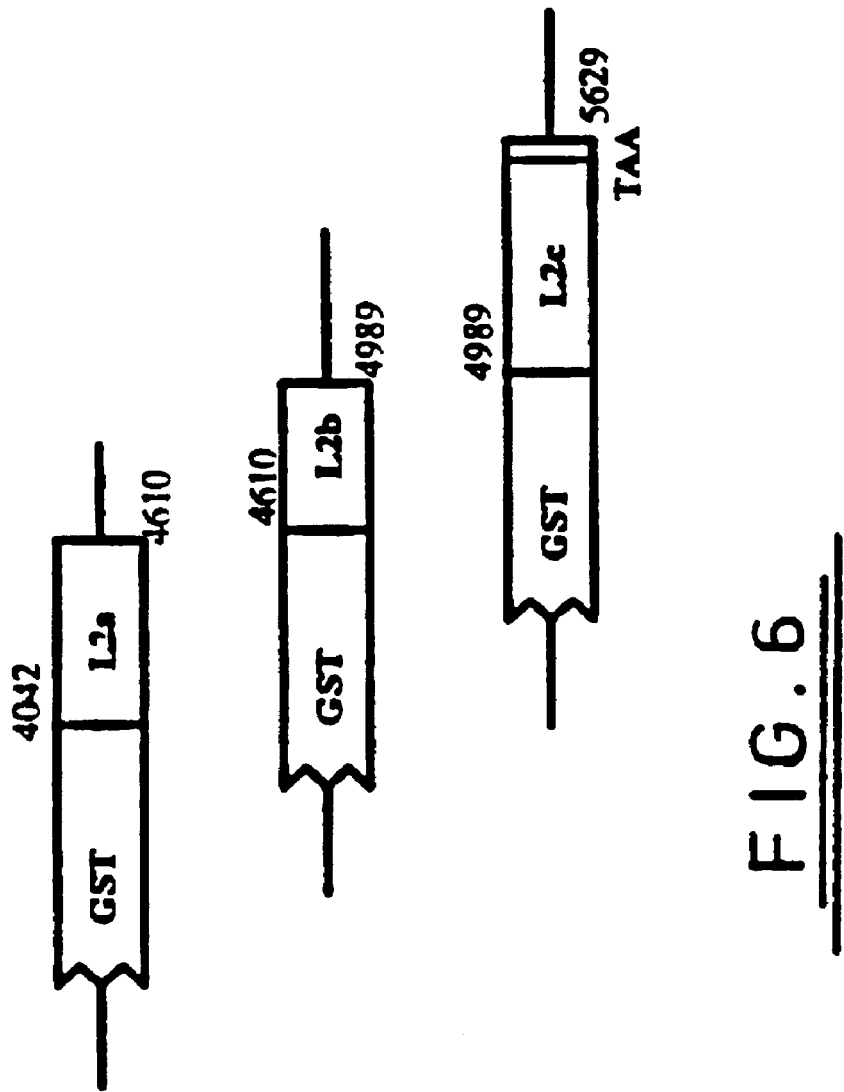

FIG. 6: shows pGEX bacterial expression vectors including L2a, L2b and L2c: and

FIG. 7: Shows the amino acid sequences for the three BPV-4 L2a epitopes of FIG. 5B.

EXAMPLE 1

Expression and Production of Recombinant L2 Proteins

Plasmid pGEX containing the gluthathione-S-transferase (GST) gene is described by Smith B. D. and Johnson K. S. Gene 67, pp31–40 (1988). Late (L) BPV-4 L2 ORF was molecularly cloned in three fragments into pGEX to form the bacterial expression vectors shown in FIG. 6. The three fragments L2a, L2b and L2c were cloned as three Dde 1 fragments as follows:

(i) 5' end fragment (nt 4042 to 4610) encoding the N-terminus of the BPV-4 L2 protein from amino acid 11 to amino acid 200 in pGEX2T.

(ii) a middle fragment, (nt 4610 to 4989) encoding from amino acid 201 to amino acid 326 in pGEX3X and (iii) a 3' end fragment (nt 4989 to 5629) encoding the C terminus from anino acid 327 to amino acid 524 in pGEX3X.

The recombinant plasmids, pGEX2T L2a, pGEX3X L2b and pGEX3X L2c were transfected into *E. coli* JM109 and the bacteria were then grown to mid-log phase in L-broth (Gibco BRL) supplemented with 100 μg/ml ampicillin. They were induced to express the glutathione-S-transferase fusion protein by the addition of 100 μg/ml (Isopropyl-b-D-Thiogalactopyronoside, supplied by BioFine, Ipswich) (IPTG) for 1 to 4 hours. Glutathione-S-transferase-L2a, -L2b, and -L2c were prepared in bulk by pelleting inclusion bodies from bacteria suspended in lysozyme buffer (25% sucrose, 10 mM-MgCl$_2$, 50 mMTris-HCl pH 8.0, 1 mg/ml lysozyme) containing DNase 1 at 300 μg/ml and deoxycholate at 1 mg/ml, followed by washing in 0.5% Triton X 100/10 mM-EDTA, pH 8.0. Yields were 2–3 mg/g wet weight bacteria and 50 to 70% purity was achieved. In all cases proteins were suspended by boiling and sonication in 5% SDS, 5 mM-2-mercaptoethanol, 50 mM-Tris-Hcl pH 8.0, prior to vaccination.

EXAMPLE 2

Vaccinations

1) Serum Antibodies Following Inoculation with Mixture 6 L2a, L2b and L2c

Calves were inoculated with a cocktail of L2a (N terminal portion of BPV-4-GST fusion protein), L2b (middle portion of BPV-4-GST fusion protein) and L2c (C-terminal portion of BPV-4-GST fusion protein). Immune sera from these animals were analysed for antibodies against the N-terminal (L2a), the middle portion (L2b) and the C-terminus (L2c) of the vaccine protein (i.e. the cocktail) at different times after vaccination and after challenge to determine the immunologically active portion of the protein. First, sera were analysed that had been collected four weeks after viral challenge. All sera had antibodies to L2c but not to L2a or l2b (FIG. 1). For this reason it was assumed that the immunogenic epitope lay within the L2c portion, and this portion was selected for further vaccination studies.

ii) Inoculation with L2c Fragment

Twelve calves were then inoculated with L2c fusion protein (C-terminus) with 12 calves used a controls. Each inoculated animal received 2 inoculations administered four weeks apart, of 330 μg protein in aluminum salts (equal volumes of 3% aluminium hydroxide and 2% aluminium phosphate in a gel—obtained from Intervet, UK) as adjuvant. Two weeks after the second inoculation ("the booster") all animals were challenged with $10^{11}$ particles of BPV-4 in the palate at 10 sites ($10^{10}$ particles per site). After challenge the animals were inspected at four week intervals over a period of twelve weeks. L2c failed to protect animals from BPV-4 challenge (FIG. 2), although it elicited both a cellular and a humoral response.

(iii) Further Serum Antibody Studies

Samples of the immune sera were analysed for antibodies to L2a, L2b and L2c two days, seven days and fourteen days after the second vaccination (boost), and two days after viral challenge. Antibodies to L2b were hardly detected at any time point; antibodies to L2a were present in high titre after vaccination and before challenge but the titre decreased dramatically soon after challenge (FIG. 3: Table 1).

iv) Successful Treatment with L2a

Eight calves were then inoculated with L2a protein (N-terminus) with 10 calves as control. Each animal was inoculated and challenged as described hereinabove for the L2c fusion protein. All the L2a vaccinated animals were resistant to BPV-4 infection (FIG. 4). Thus, it was surprisingly found that the L2 immunogenic epitope lay within the N-terminal L2a portion.

EXAMPLE 3

Epitope Mapping (ELISA)

Further studies were then made to map the eptope within the l2a fragment, following the general inoculation strategy described in Example 2. Synthetic peptides were obtained from Alta Bio-science, University of Birmingham which are generally twenty amino acid residues long, overlapping by ten amino acid residues, which spanned the BPV-L2 N-terminal protein. The peptides in 10 mM sodium carbonate buffer pH 9.6 were coated on microtitre plates at 2 μg/well. The plates were left at 4° C. overnight. Plates were blocked with 10% goat serum, 5% nonfat dried milk, 0.5% Tween in phosphate buffered saline (PBS) for 1 hour at 37 C. Plates were washed six times with 0.5% Tween in PBS using an automated plate washer. Immune bovine sera at a dilution of 1:2 or 1:10 were added to each well and left overnight at 37° C. Plates were washed six times as above. Goat anti-bovine lgG, conjugated to alkaline phosphatase (DynaTech) was added for 1 hour at 37° C. at 1:500 dilution. The plates were washed six times as above and developed using an alkaline phosphate substrate kit (Biorad), using 3-hydroxyl-2-naphtonic acid 2,4 dimethylanilide/4-chloro-O-toluidine-1,5 diazonium naphthalene disulphonate as substrate and read at 405 nm using a Biorad plate reader. The results are shown in FIG. 5.

Sera from L2a vaccinated animals were analysed for their antibody response to the peptides spanning the N-terminus of L2.

The results are shown in FIG. 5A (immune sera one week post-boost) and in FIG. 5B (two weeks post-boost and immediately prior to viral challenge).

A group of eight cows were treated, which are numbered in the range 257 to 287 in FIG. 5A and are represented by various symbols in FIG. 5B. The twenty 20 amino acid peptides (from amino acid 1–15 through to 193–197; some of the peptides having in fact less than 20 amino acids) shown in FIG. 5A correspond to the twenty peptides numbered 1 to 20 in FIG. 5B.

FIG. 5A shows at one week post-boost the presence of an epitope at peptide 11 (amino acid 101–120). As shown in FIG. B at two weeks post-boost a response to three epitopes has appeared; these being peptide 11 (aa 101–120), peptide 14 (aa 132–151) and peptide 16 (aa 151–171). The sequences of these three peptide epitopes is given in FIG. 7 (the portions showing homology with HPV's are underlined). These three peptides were recognised by the immune sera and represent the immunodominant B-cell epitopes in the N-terminus of the protein. Peptides 11 and 16 encode the major epitopes and peptide 14 encodes a minor epitope.

TABLE 1

IMMUNODOMINANT EPITOPES IN BPV-4 PROTEINS

| Vaccine<br>L2 | Responder animals | |
|---|---|---|
| | 7 days<br>after boost | 2 days<br>after challenge |
| L2a N-ter(aa 11–200) | 6/6 | 0/6 |
| L2b middle(aa 201–326) | 0/6 | 0/6 |
| L2c C-ter(aa 327–524) | 1/6 | 6/6 |

What is claimed is:

1. An immunogenic peptide for the treatment of papillomavirus infection, wherein the peptide is: (a) a peptide from 10–30 amino acid residues in length having a sequence corresponding to a sequence from the N terminal amino acids 11–200 of papillomavirus L2 protein, (b) a peptide of 10–30 amino acid residues in length with at least 30% identity with the sequence from (a) as determined using the BESTFIT program, or (c) a peptide as defined in either (a) or (b) which is conjugated or fused to a protein or peptide other than a papillomavirus L2 protein or peptide.

2. The peptide of claim 1, wherein the peptide as defined in (a) or (b) of claim 1 is 10 to 21 amino acids long.

3. The peptide of claim 1 wherein the immunogenic amino acid sequence comprises amino acid residues 10 to 19 of SEQ ID NO:1, or amino acid residues 1–14 of SEQ ID NO:3.

4. The peptide of claim 1 wherein the peptide as defined in (a) of claim 1 is: SEQ ID NO:1, SEQ ID NO:2, SEQ ID NO:3, SEQ ID NO:4, SEQ ID NO:5, SEQ ID NO:6, SEQ ID NO;7, SEQ ID NO:8, SEQ ID NO:9, SEQ ID NO:10, SEQ ID NO:11, SEQ ID NO:12, or SEQ ID NO:13.

5. The peptide of claim 1 produced by recombinant DNA techniques.

6. The peptide of claim 1 produced synthetically.

7. A nucleotide sequence encoding the immunogenic peptide of claim 1.

8. An immunogenic formulation comprising an immunogenic peptide of claim 1 or a nucleotide sequence encoding the peptide.

9. The peptide of claim 1, wherein the peptide as defined in (a) or (b) of claim 1 is conjugated or fused to keyhole limpet haemocyanin.

10. The peptide of claim 1, wherein peptide (a) or (b) as defined in claim 1 is conjugated or fused to glutathione-S-transferase.

11. An immunogenic composition comprising an N-terminal L2 protein fragment, wherein said L2 protein fragment consists of 10–30 contiguous amino acid residues from residues 11–200 of papilomavirus L2 conjugated or fused to a protein or peptide other than a papillomavirus L2 protein or peptide, and the L2 protein fragment has a sequence as set forth as SEQ ID NO;1, SEQ ID NO;2, SEQ ID NO:3,S EQ ID NO:4, SEQ ID NO;5, SEQ ID NO:6, SEQ ID NO:7, SEQ ID NO:8, SEQ ID NO:9, SEQ ID NO:10, SEQ ID NO:11, SEQ ID NO:12, OR SEQ ID NO:13.

12. The composition of claim 11, wherein the L2 protein fragment has a length of 10–21 contiguous amino acid residues.

13. The composition of claim 11, further comprising a pharmaceutical carrier.

14. The composition of claim 11, wherein the protein fragment further comprises a fusion protein that includes the L2 protein fragment.

15. A method of treating a mammal against papillomavirus infection comprising administering to said mammal an immunogenic peptide of claim 1 or a nucleotide sequence encoding the peptide.

16. The method of claim 15 wherein the mammal is a human.

17. The method of claim 15 wherein the mammal is bovine.

18. A method of treating a mammal against papillomavirus infection comprising administering to the mammal the composition of claim 11.

19. A method according to claim 18, wherein the administration is parenteral.

20. A method according to claim 18, wherein the composition is administered as a suppository.

21. A method according to claim 18, wherein the composition is administered as a pessary.

* * * * *

UNITED STATES PATENT AND TRADEMARK OFFICE
CERTIFICATE OF CORRECTION

PATENT NO. : 6,174,532 B1
DATED : January 16, 2001
INVENTOR(S) : Maria Saveria Campo and William Fleming Hoggan Jarrett It is certified that error appears in the above-identified patent and that said Letters Patent is hereby corrected as shown below:

Column 2,
Line 58, (page 4, line 24 of the application), "NO:3 reading" should read -- NO:3) reading --.

Column 3,
Line 37, (page 2 of the Amendment dated May 12, 1997), "sequences (I) and (III)" should read -- SEQ ID NO:1 AND SEQ ID NO:3 --.

Column 4,
Line 37, (page 7, line 24 of the application), "deltions" should read -- deletions --.

Column 5,
Line 14, (page 3 of the Amendment dated May 12, 1997), "ten HPV SEQ" should read -- ten SEQ --.
Line 48, (page 10, line 12 of the application), "pophylactic" should read -- prophylactic --.

Signed and Sealed this

Thirtieth Day of October, 2001

Attest:

NICHOLAS P. GODICI
Attesting Officer
Acting Director of the United States Patent and Trademark Office

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH:20 amino acids
      (B) TYPE: amino acid
      (D) TOPOLOGY: linear (ii) MOLECULE TYPE: peptide (xi) SEQUENCE DESCRIPTION: SEQ ID NO: 1:

```
Thr Gly Val Pro Ile Asp Pro Ala Val Pro
1               5                   10

Asp Ser Ser Ile Val Pro Leu Leu Glu Ser
                15                  20
```

(2) INFORMATION FOR SEQ ID NO: 2:

(i) SEQUENCE CHARACTERISTICS:
      (A) LENGTH: 20 amino acids
      (B) TYPE: amino acid
      (D) TOPOLOGY: linear (ii) MOLECULE TYPE: peptide (xi) SEQUENCE DESCRIPTION: SEQ ID NO: 2:

```
Gly Ala Glu Ile Glu Ile Ile Ala Glu Val
1               5                   10

His Pro Pro Val Tyr Glu Gly Pro Glu
                15                  20
```

(2) INFORMATION FOR SEQ ID NO: 3:

(i) SEQUENCE CHARACTERISTICS:
      (A) LENGTH: 21 amino acids
      (B) TYPE: amino acid

```
        (D) TOPOLOGY: linear (ii) MOLECULE TYPE: peptide (xi) SEQUENCE DESCRIPTION: SEQ ID NO: 3:

Val Thr Ile Gly Asp Ile Glu Glu Pro Pro
1               5                   10

Ile Leu Glu Val Val Pro Glu Thr His Pro
                15                  20

Thr (2) INFORMATION FOR SEQ ID NO: 4:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO: 4:

Thr Asp Pro Ser Ile Val Thr Leu Ile Glu
1               5                   10

(2) INFORMATION FOR SEQ ID NO: 5:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO: 5:

Ser Asp Pro Ser Ile Val Ser Leu Val Glu
1               5                   10

(2) INFORMATION FOR SEQ ID NO: 6:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO: 6:

Ser Asp Pro Ser Ile Val Ser Leu Ile Glu
1               5                   10

(2) INFORMATION FOR SEQ ID NO: 7:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO: 7:

Ser Asp Pro Ser Ile Val Ser Leu Ile Glu
1               5                   10

(2) INFORMATION FOR SEQ ID NO: 8:

(i) SEQUENCE CHARACTERISTICS:
        (A) LENGTH: 10 amino acids
```

```
        (B) TYPE: amino acid
        (D) TOPOLOGY: linear (ii) MOLECULE TYPE: peptide (xi) SEQUENCE DESCRIPTION: SEQ ID NO: 8:

Ser Asp Pro Ser Ile Val Ser Leu Ile Glu
1               5                   10

(2) INFORMATION FOR SEQ ID NO: 9:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO: 9:

Ile Thr Ser Ala Gly Thr Thr Thr Pro Ala Val Leu Asp Ile
1               5                   10

(2) INFORMATION FOR SEQ ID NO: 10:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO: 10:

Ile Thr Thr Ser Thr Asp Thr Thr Pro Ala Ile Leu Asp Ile
1               5                   10

(2) INFORMATION FOR SEQ ID NO: 11:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO: 11:

Ile Thr Ser Ser Glu Ser Thr Thr Pro Ala Ile Leu Asp Val
1               5                   10

(2) INFORMATION FOR SEQ ID NO: 12:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO: 12:

Ile Thr Ser Ser Glu Thr Thr Thr Pro Ala Ile Leu Asp Val
1               5                   10

(2) INFORMATION FOR SEQ ID NO: 13:

(i) SEQUENCE CHARACTERISTICS:
        (A) LENGTH: 14 amino acids
        (B) TYPE: amino acid
        (D) TOPOLOGY: linear (ii) MOLECULE TYPE: peptide
```

(xi) SEQUENCE DESCRIPTION: SEQ ID NO: 13:

Ile Thr Ser Ser Glu Thr Thr Thr Pro Ala Ile Leu Asp Val
1               5                   10